United States Patent
Knobl et al.

(10) Patent No.: US 10,433,808 B2
(45) Date of Patent: Oct. 8, 2019

(54) ROTARY JOINT HAVING A CAPACITIVE DATA LINK WITH MODULAR SUPPORT

(71) Applicant: SCHLEIFRING GMBH, Furstenfeldbruck (DE)

(72) Inventors: Horst Knobl, Schongau (DE); Kathrin Wörl, Egenhofen (DE)

(73) Assignee: SCHLEIFRING GMBH, Fürstenfeldbruck (DE)

( * ) Notice: Subject to any disclaimer, the term of this patent is extended or adjusted under 35 U.S.C. 154(b) by 0 days.

(21) Appl. No.: 15/985,407

(22) Filed: May 21, 2018

(65) Prior Publication Data

US 2018/0333130 A1    Nov. 22, 2018

(30) Foreign Application Priority Data

May 22, 2017 (EP) .................... 17172301

(51) Int. Cl.
| | |
|---|---|
| *A61B 6/00* | (2006.01) |
| *H01R 39/08* | (2006.01) |
| *H04B 5/00* | (2006.01) |
| *A61B 6/03* | (2006.01) |

(52) U.S. Cl.
CPC .............. *A61B 6/56* (2013.01); *A61B 6/032* (2013.01); *A61B 6/035* (2013.01); *H01R 39/08* (2013.01); *H04B 5/0012* (2013.01); *H04B 5/0031* (2013.01); *H04B 5/0037* (2013.01)

(58) Field of Classification Search
USPC ........................................ 455/41.1
See application file for complete search history.

(56) References Cited

U.S. PATENT DOCUMENTS

| | | | |
|---|---|---|---|
| 6,798,309 B2 | 9/2004 | Lohr et al. | |
| 2006/0256634 A1* | 11/2006 | Krumme | A61B 6/56 365/202 |
| 2008/0279302 A1* | 11/2008 | Granger | A61B 6/56 375/285 |
| 2009/0091403 A1* | 4/2009 | Hemmerlein | G08C 15/08 333/172 |
| 2013/0214614 A1* | 8/2013 | Krumme | A61B 6/56 307/104 |
| 2016/0127052 A1 | 5/2016 | Steffens | |
| 2016/0211822 A1* | 7/2016 | Weithmann | A61B 6/56 |

* cited by examiner

*Primary Examiner* — Ganiyu A Hanidu
(74) *Attorney, Agent, or Firm* — Yakov S. Sidorin; Quarles & Brady LLP

(57) ABSTRACT

A set of rotary joint components containing stationary part(s) and rotatable part(s) repositionable with respect to each other. The stationary part has a stationary base with means for holding a stationary carrier into a circular-shaped form. The stationary carrier holds at least a stationary transmitter coupler of a contactless data link, such as a strip line. The stationary carrier is made of sheet metal or plastic material, and therefore can easily be prepared on a plane work bench before it is bent to a ring shape.

12 Claims, 6 Drawing Sheets

ROTARY JOINT HAVING A CAPACITIVE DATA LINK WITH MODULAR SUPPORT

CROSS-REFERENCE TO RELATED APPLICATIONS

This application claims priority from and benefit of the pending European Application No. 17172301.8 filed on May 22, 2017, the disclosure of which is incorporated herein by reference.

BACKGROUND

1. Field of the Invention

The invention generally relates to sliprings and contactless data links and, in particular, to those sliprings and contactless data links that may be used in Computed Tomography (CT) scanners.

2. Description of Relevant Art

In computed tomography (CT) scanners, usually large sliprings having a diameter of approximately 1 meter or more are required. The sliding tracks must be held at a supporting structure while insulating the sliding tracks from each other and from other machine parts. Furthermore, capacitive data links configured for coupling data with high data rates from a rotating part to a stationary part are typically provided.

U.S. Pat. No. 5,054,189 discloses a slipring having a body made of insulating material with pre-machined grooves, into which a conductive sliding track is rolled.

U.S. Pat. No. 5,734,218 discloses a drum-shaped slipring having a preformed insulating body with grooves, into which sliding tracks are pressed. The body requires a rigid backing member as mechanical support.

A capacitive rotary joint for CT scanners is disclosed in U.S. Pat. No. 5,600,697. A large diameter rotating ring carries a differentially-driven strip coupler guiding a signal along this circumference of the ring. At the stationary side, there is a capacitive coupler picking up the signal from the near field of the strip coupler. The receiving coupler includes two couplers that are held orthogonally to the transmission coupler. To obtain a sufficient coupling efficiency and, therefore, a sufficient signal level at the receiver, the coupler must be mounted in close proximity to the strip coupler.

A bidirectional capacitive coupler is disclosed in US 2013/0214614. Here, the channels that establish communication from the rotating to the stationary side and vice versa are interleaved. The datalink transmitters are mounted on a comparatively large, solid and, therefore, expensive body made of insulating material.

These embodiments have the practical disadvantage in that they require comparatively solid insulating bodies, which bodies further require a significant amount of insulating material or additional rigid backing. Another disadvantage is the comparatively big size of the insulating body, which renders handling and manufacturing of the insulating body difficult and expensive.

SUMMARY

The embodiments provide a rotary joint component or a slipring component having a capacitive data link in a comparatively lightweight and simple assembly.

In one embodiment, a rotary joint component includes a stationary part and a rotatable part. The rotatable part is configured to be rotatable against the stationary part. In a CT (computed tomography) scanner, a gantry has a rotatable part which rotates around the patient. The rotatable part requires a supply of power from the stationary part, which is delivered by the rotary joint. The rotary joint further delivers data from the rotatable part to the stationary part. Therefore, the direction of a preferred data link is that from the rotatable to the stationary part. In an alternate embodiment, there may be a data transfer arranged from the stationary to the rotatable part, or in both directions. The implementation in which the data transfer is configured in both directions may provide, for example, a data flow from an image detector of the rotatable gantry to a stationary part, and the flow of control data from the stationary part to the rotatable part of the gantry.

In a related embodiment, the rotatable part contains a rotatable base that is configured for holding rotatable components, such as, for example, at least one rotatable receiver coupler. The stationary part includes a stationary base, which holds at least one stationary transmitter coupler. The positions of the stationary transmitter coupler and the rotatable receiver coupler are appropriately adjusted such that the stationary transmitter coupler is capacitively coupled to the at least one rotatable receiver coupler, to enable the capacitive transfer of data.

Below, the reference is made to a general coupler for capacitive coupling. It is preferred, if these general couplers have pairs of couplers including a transmitter coupler and a receiver coupler. Most preferably, the transmitter coupler is a line or a strip line extended along the way of movement between the couplers. In a specific case of a rotatable movement, this means that the transmitter coupler is arranged circularly (to form a circular shape) around the center axis of rotation. The receiver coupler may be presented either by a line, a strip line, or a simple capacitive coupling pad, which are preferably terminated with the characteristic impedance, to achieve capacitive coupling to the transmitter coupler.

At least one rotatable transmitter coupler and/or at least one stationary transmitter coupler may be separated radially by a distance of less than 10 mm (preferably less than 5 mm, and most preferably less than 3 mm) from the facing at least one stationary receiver coupler and/or the at least one rotatable receiver coupler.

Additional components are required for a capacitive data transfer, such as a data transmitter (which preferably is at the side of the rotatable part) and a data receiver (which preferably is at the side of the stationary part).

The stationary transmitter coupler is mounted to or held by a stationary carrier. This stationary carrier includes a circularly-shaped sheet of metal or plastic that is further held by the stationary base. The sheet may have a thickness between about 0.2 mm and 3 mm. (For example, a metal sheet may have a thickness between about 0.3 mm and 1.5 mm, whereas a plastic sheet may have a thickness between about 1.5 mm and 3 mm). A material of the metal sheet may include at least one of steel, stainless steel, brass, copper, or any combination thereof. A material of the plastic sheet material may include Polycarbonate, Polyethylene or another suitable material, with or without fiber reinforcement.

As the stationary carrier includes sheet material, it can be manufactured easily, by, for example, cutting a rectangular sheet of metal or plastic material having the right size (with the length corresponding to the circumference of the later arc shape, and the width corresponding to the required height, matching in dimension to the stationary transmitter coupler). The sheet metal or plastic material acquires the required stiffness and/or mechanical stability as a result of being mounted to the stationary base. To the so mounted sheet, at least one stationary transmitter coupler may be attached, for example with the use of a double-sided adhesive tape. As the sheet is a planar sheet, the required steps may easily be carried out on a plane work bench: it is not necessary to handle a complex circular structure.

The stationary base may have specific means configured to hold the stationary carrier that includes a sheet metal or plastic in a circular shape. Preferably, the stationary carrier may be fixed to the stationary base with screws, bolts or similar means. The stationary carrier may be glued, injection-molded or held otherwise to the stationary base. The stationary carrier may be press-fitted into a groove in the stationary base, it may be bolted or screwed to the inner or outer diameter of a stationary base. Handling of two separate components, such as the stationary carrier and the stationary base, is comparatively simple, because both are substantially flat (planar) components. As such, these components may be shipped easily and assembled later at the final destination. Such design also offers larger manufacturing flexibility. For example, different coupler configurations may be preassembled on stationary carriers and before finishing the slipring, one of these stationary carriers may be selected in assembly of the desired configuration.

The use of sheet metal in the process of making the stationary carrier also provides electrical and/or electromagnetic shielding to the data link and, specifically, to the transmitter coupler. The appropriate shielding may also be provided if a plastic sheet material with a metallized surface is used. Alternatively, an aluminum-plastic composite material may be cut as rectangular sheet and bent into a circular shape for use as carrier.

At least one rotatable receiver coupler and/or at least one stationary receiver coupler may be galvanically connected to the corresponding stationary carrier, which further may be galvanically connected to the corresponding stationary base.

There may be at least one sliding track arranged at the rotatable part.

Such sliding track(s) may be used to establish a galvanic contact together with sliding brushes to provide a galvanic connection between the stationary and rotatable parts. Such galvanic connection may be utilized to supply electrical power from the stationary to the rotatable part.

At the stationary base, there may be present a stationary electronic module support configured to support and hold a stationary electronic module, which provides connecting means (such as connectors and/or amplifiers and/or transmitters and/or receivers), which may be connected to at least one stationary transmitter line and/or stationary receiver line.

Furthermore, the stationary part may provide connecting means, such as connectors and/or amplifiers and/or transmitters and/or receivers, which may be connected to at least one stationary transmitter line and/or stationary receiver line. The rotatable electronic module and/or the stationary electronic module may also be connected to at least one of the sliding tracks. Such connection may be used for grounding and/or for supplying power or other signals to the electronic modules.

BRIEF DESCRIPTION OF THE DRAWINGS

In the following, the examples of implementation of the idea of the invention is described without limitation of the general inventive concept and with reference to the drawings.

Various modifications and alternative forms deviating from the discussed specific embodiments remain within the scope of the invention. The presented drawings and detailed description are not intended to limit the invention to the particular form disclosed, but on the contrary, the intention is to cover all modifications, equivalents and alternatives falling within the spirit and scope of the present invention as defined by the appended claims.

DETAILED DESCRIPTION

Figure 1:
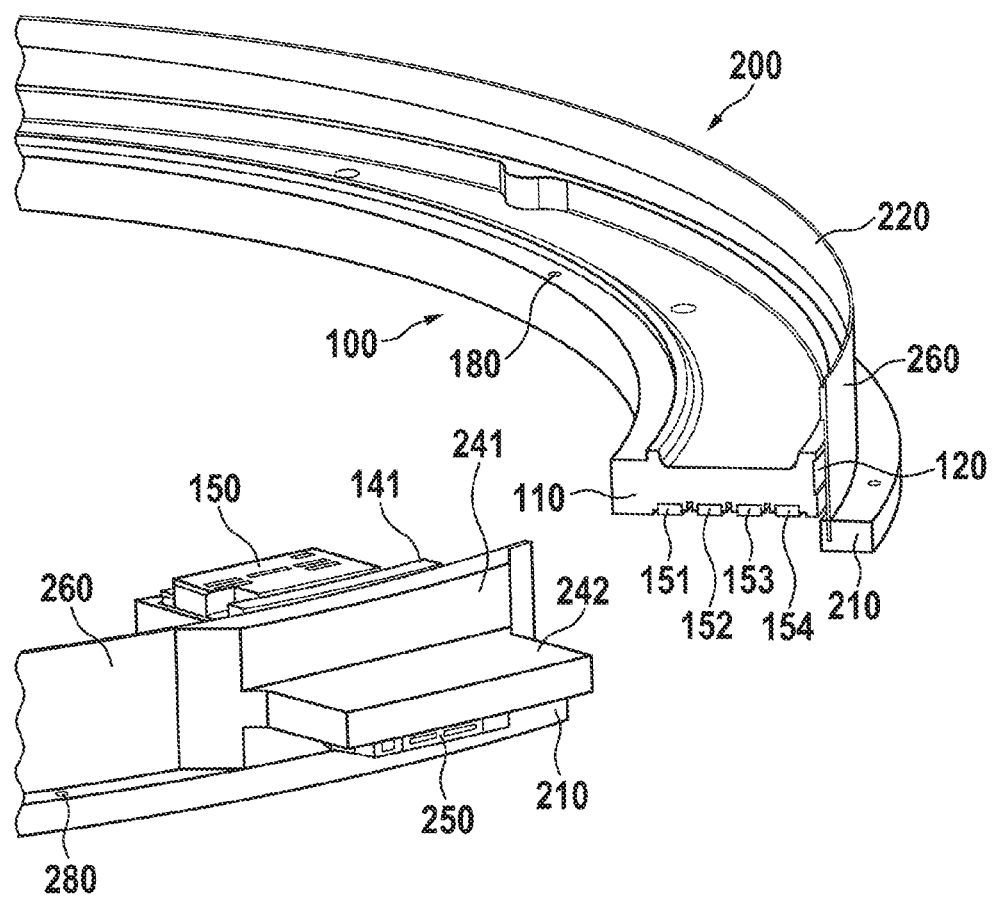
FIG. 1 shows a first embodiment.

FIG. 1 demonstrates, the first embodiment, which relates to a circular embodiment of the basic components. In this FIG. 1 and in some of the following Figures, ring-shaped parts are shown with a cut-out section, to show inner structure of the ring-shaped parts. A rotatable part 100 includes a rotatable base 110, which may support a rotatable transmitter coupler 120 (formed as a strip line, for example). The rotatable base is further shown to support a plurality of sliding tracks 151, 152, 153, and 154. (In a related implementation, any other number of sliding tracks may be present, as required.) There is also shown a rotatable electronic module 150, mounted to a rotatable electronic module support 141. For mounting the rotatable part for example to a rotatable part of a CT scanner, a plurality of rotatable screw holes 180 may be used.

This FIG. 1 also shows a stationary part 200 (which has a stationary base 210 holding a stationary carrier 260). On the stationary carrier 260, there is a stationary transmitter coupler 220, which may be configured as a transmission line. A stationary electronic module 250 is supported by or mounted to a stationary electronic module support (which may comprise a first support component 241 and a second support component 242). For mounting the stationary part, for example, to a stationary part of a CT scanner, a plurality of stationary screw holes 280 may be used.

Figure 2:
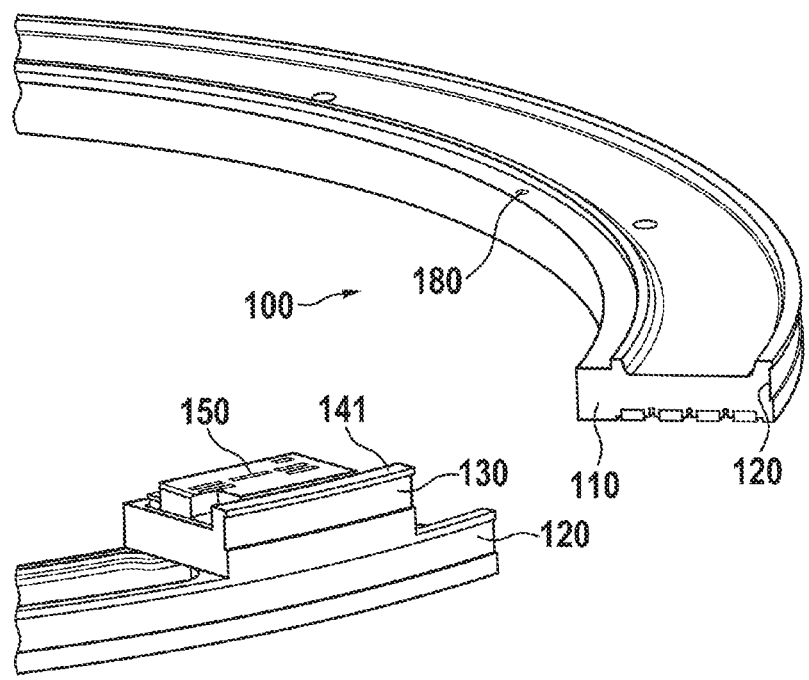
FIG. 2 shows the rotatable part without stationary part.

In FIG. 2, the rotatable part 100 is shown without the stationary part 200. FIG. 2 illustrates additional details of the rotatable transmitter coupler 120, which may be mounted in a groove, are shown. Furthermore, the rotatable receiver coupler 130 is shown, which preferably is held by the rotatable electronic module support 141.

Figure 3:
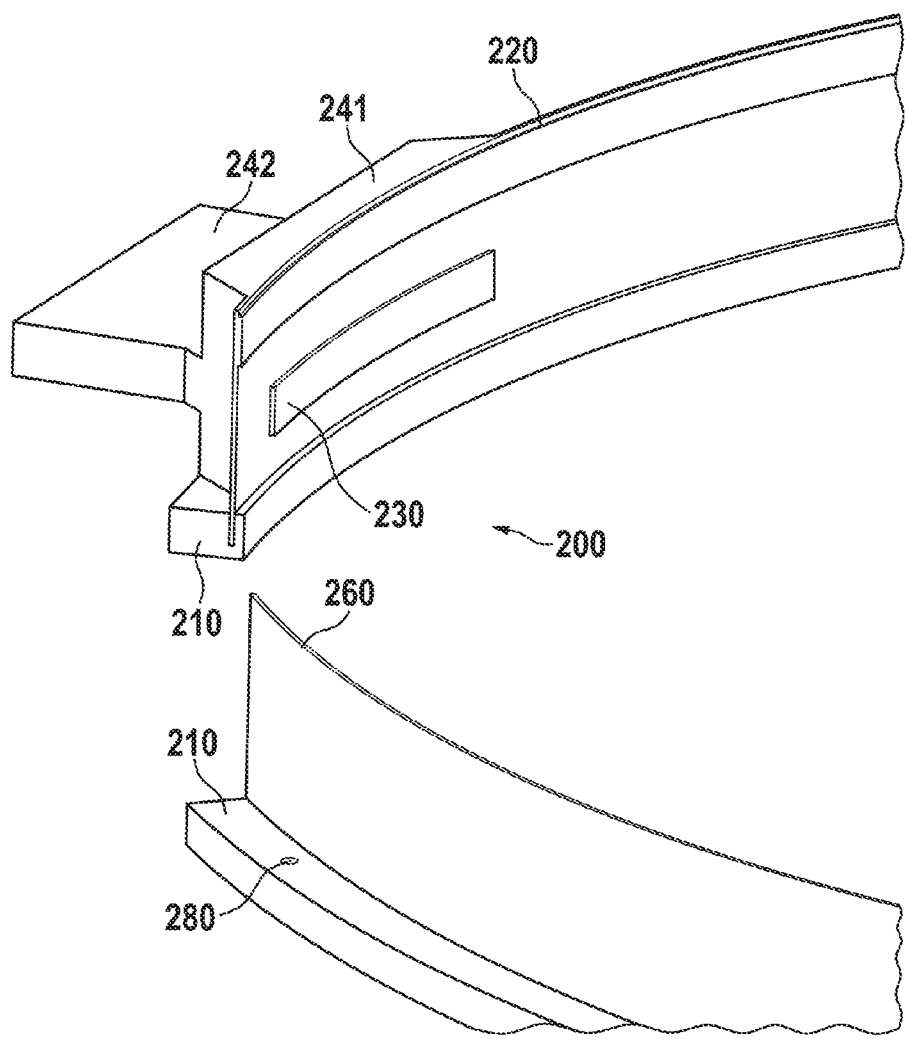
FIG. 3 shows the stationary part from the inner side.

In FIG. 3, the stationary part 200 is illustrated from the inner side. Here, the stationary receiver coupler 230 is shown, which may be held by the stationary electronic module support 241, 242. The width of the stationary carrier 260 depends on the number of data transmission links and typically is in the range from about 20 mm to about 100 mm.

Figure 4:
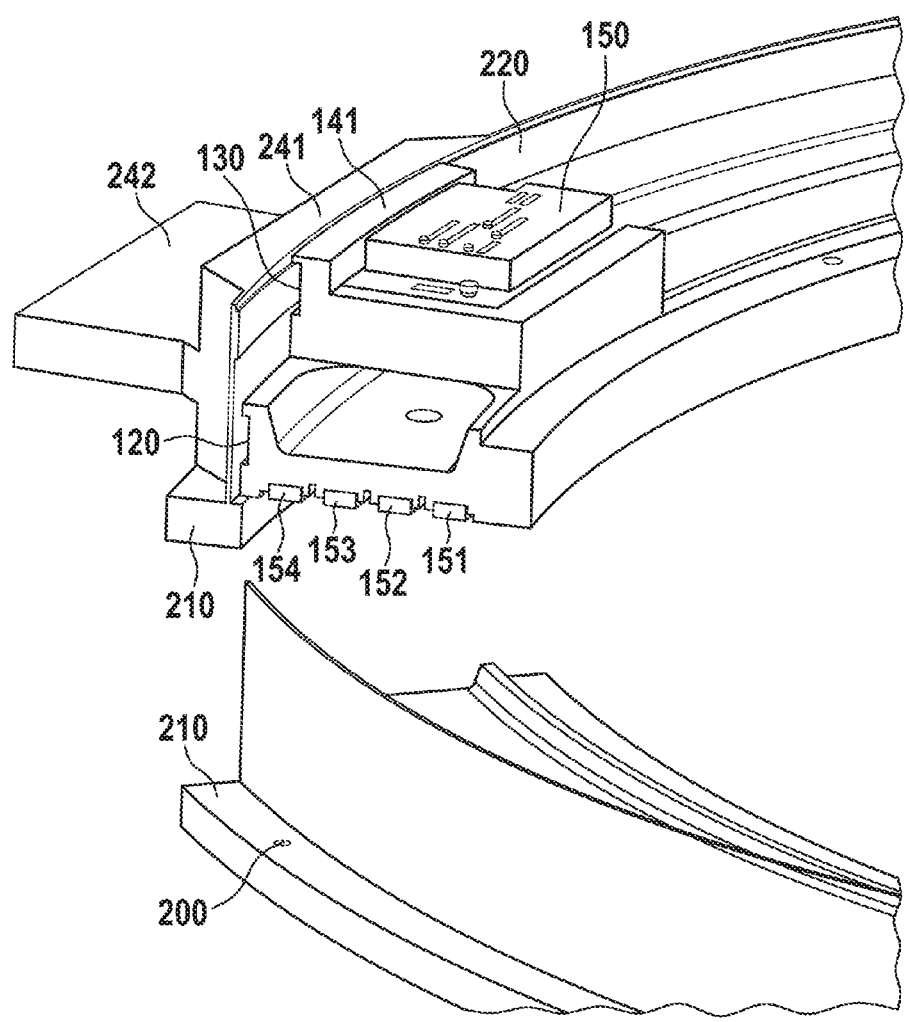
FIG. 4 shows further details of an embodiment.

In FIG. 4, further details are illustrated and, specifically, the interaction between the stationary transmitter coupler 220 and the rotatable receiver coupler 130, which runs on the same track such that the distance between the stationary transmitter coupler 220 and the rotatable receiver coupler 130 remains substantially short (below 10 mm, more preferably below 5 mm, and most preferably below 3 mm).

Figure 5:
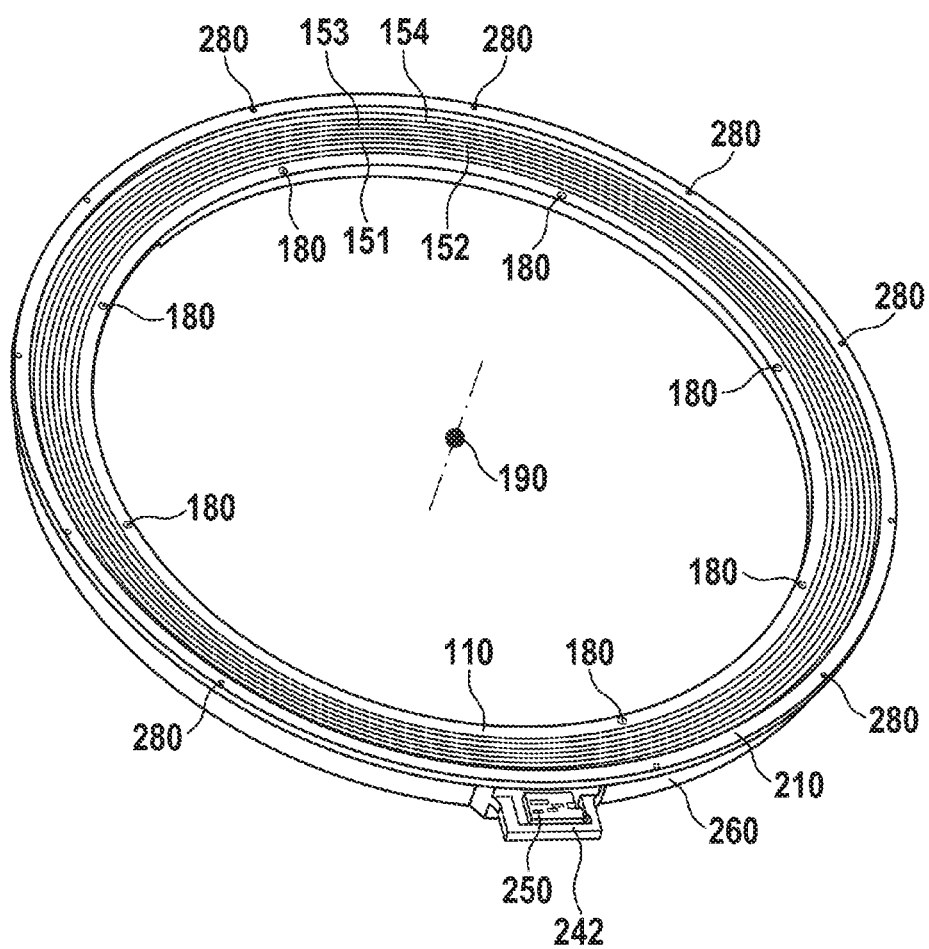
FIG. 5 shows a full view of an embodiment.

In FIG. 5, the rotatable part 100 and the stationary part 200, with all associated components, are shown in full view. The axis of rotation 190 passes through the center at a right angle with respect to a plane defined by the rotatable base 110.

Figure 6:
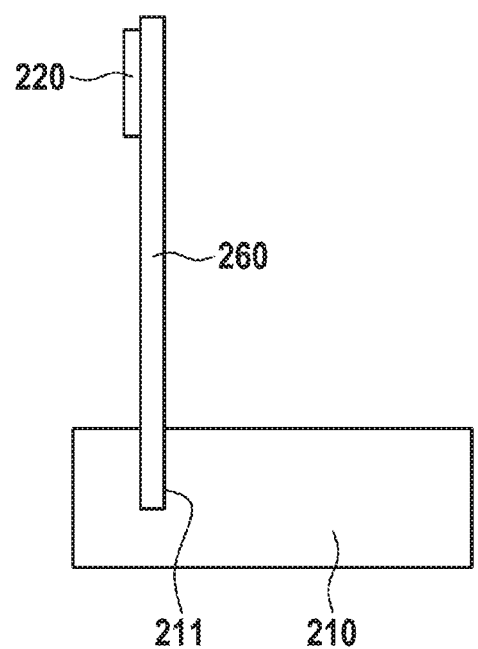
FIG. 6 shows a detail of a stationary carrier mounted to a stationary base.

FIG. 6 provides details of the mounting of the stationary carrier into the stationary base. Preferably, the stationary base 210 has a slot 211 dimensioned to hold the stationary carrier 260.

A person skilled in the art will readily appreciate that embodiments of this invention provide sliprings and contactless data links. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 rotatable part
110 rotatable base
120 rotatable transmitter coupler
130 rotatable receiver coupler
141 rotatable electronic module support
150 rotatable electronic module
151, 152, 153, 154 sliding tracks
180 rotatable screw hole
190 axis of rotation
200 stationary part
210 stationary base
211 slot
220 stationary transmitter coupler
230 stationary receiver coupler
241, 242 stationary electronic module support
250 stationary electronic module
260 stationary carrier
280 stationary screw hole

The invention claimed is:

1. A rotary joint component comprising a stationary part and a rotatable part configured to rotate against the stationary part,
   the rotatable part including a rotatable base holding at least one rotatable receiver coupler and at least one rotatable transmitter coupler,
   the stationary part including a stationary base holding at least one stationary transmitter coupler and at least one stationary receiver coupler,
   wherein the at least one stationary transmitter coupler is capacitively coupled to the at least one rotatable receiver coupler,
   wherein the at least one stationary transmitter coupler is mounted to a stationary carrier containing a circularly-shaped sheet of metal or plastic, said sheet being held by the stationary base to have the sheet and at least one stationary transmitter extend transversely to the stationary base; and
   wherein the at least one rotatable transmitter coupler is separated radially from the at least one stationary receiver coupler by a first radial distance.

2. The rotary joint component according to claim 1, wherein the rotatable part comprises at least one sliding track held by the rotatable base.

3. The rotary joint component according to claim 1, wherein the stationary carrier is held within a slot or groove of the stationary base.

4. The rotary joint component according to claim 1, wherein
   the stationary part holds the at least one stationary receiver coupler on said sheet to extend transversely to the stationary base, wherein the at least one stationary receiver coupler is capacitively coupled to the at least one rotatable transmitter coupler;
   and
   the at least one rotatable receiver coupler is separated radially from the at least one stationary transmitter coupler by a second radial distance.

5. The rotary joint component according to claim 1, wherein at least one of the at least one rotatable transmitter coupler and the at least one stationary transmitter coupler includes a line or a stripline terminated with a corresponding characteristic impedance.

6. The rotary joint component according to claim 1, wherein
   at least one of the at least one rotatable receiver coupler and the at least one stationary receiver coupler includes a lines, a stripline, or a pad terminated with a corresponding characteristic impedance.

7. The rotary joint component according to claim 1,
   wherein the at least one rotatable receiver coupler is separated from the at least one stationary receiver coupler by a second radial distance,
   wherein said first and second radial distances are shorter than 10 mm.

8. The rotary joint according to claim 1,
   wherein the at least one rotatable receiver coupler is separated from the at least one stationary receiver coupler by a second radial distance,
   wherein said first and second radial distances are shorter than 5 mm.

9. The rotary joint according to claim 1,
   wherein the at least one rotatable receiver coupler is separated from the at least one stationary receiver coupler by a second radial distance,
   wherein said first and second radial distances are shorter than 3 mm.

10. The rotary joint component according to claim 1, wherein
    at least one of the at least one rotatable receiver coupler and the at least one stationary receiver coupler is galvanically connected to a respectively corresponding stationary carrier, said stationary carrier being galvanically connected to a corresponding stationary base.

11. The rotary joint component according to claim 1, wherein
    the stationary carrier comprises a circularly-shaped sheet of metal that has ends connected to each other via a connection.

12. The rotary joint component according to claim 11, wherein
    the connection comprises a soldering connection or a welding connection.

* * * * *